United States Patent [19]

Roberts et al.

[11] Patent Number: 5,616,328

[45] Date of Patent: Apr. 1, 1997

[54] METHOD OF PREPARING GRAM-NEGATIVE BACTERIAL VACCINES

[75] Inventors: David S. Roberts; Donald A. Dearwester; Leroy A. Swearingin, all of Lincoln, Nebr.

[73] Assignee: Pfizer Inc., New York, N.Y.

[21] Appl. No.: 240,649

[22] PCT Filed: Nov. 13, 1992

[86] PCT No.: PCT/US92/09944

§ 371 Date: Jul. 11, 1994

§ 102(e) Date: Jul. 11, 1994

[87] PCT Pub. No.: WO93/10216

PCT Pub. Date: May 27, 1993

Related U.S. Application Data

[63] Continuation-in-part of Ser. No. 792,488, Nov. 15, 1991, abandoned.

[51] Int. Cl.[6] ............... A61K 39/112; A61K 39/108; A61K 39/10; C07K 1/00
[52] U.S. Cl. ............... 424/257.1; 424/184.1; 424/258.1; 424/240.1; 530/420; 530/412
[58] Field of Search ............... 424/257.1, 258.1, 424/184.1, 240.1; 530/420, 412

[56] References Cited

U.S. PATENT DOCUMENTS

| 4,455,297 | 6/1984 | Syukuda et al. | 424/92 |
|---|---|---|---|
| 4,465,665 | 8/1984 | Dobrescu | 424/92 |
| 4,705,686 | 11/1987 | Scott et al. | 424/92 |
| 4,789,544 | 12/1988 | Nelson et al. | 424/92 |
| 5,019,388 | 5/1991 | Brown et al. | 424/92 |
| 5,101,019 | 3/1992 | Fujita et al. | 530/420 |
| 5,536,496 | 7/1996 | Frantz . | |

OTHER PUBLICATIONS

Beecham Laboratories 1989 Atrobac 3 product literature.

*Primary Examiner*—James C. Housel
*Assistant Examiner*—N. M. Minnifield
*Attorney, Agent, or Firm*—Peter C. Richardson; Paul H. Ginsburg; Alan L. Koller

[57] ABSTRACT

There is provided by this invention a novel method of preparing Gram-negative bacterial vaccines. The method comprises providing a concentrated Gram-negative bacterial antigenic preparation, adsorbing the preparation with a mineral carrier capable of binding free-endotoxin in the antigenic preparation in an amount effective to produce optimal binding of endotoxin and antigen and diluting the adsorbed preparation for use in a vaccine. Also provided by this invention is a vaccine produced by the method of this invention. Also provided by this invention is a Gram-negative bacterial vaccine wherein the improvement comprises a concentration of mineral carrier in the vaccine which is less than 5.0% v/v. Also provided by this invention is a Gram-negative bacterial vaccine comprising a mineral carrier wherein the amount of the mineral carrier in the vaccine has been predetermined by the method of this invention. Also provided by this invention is a method of vaccinating an animal against Gram-negative bacterial infections comprising administering to the animal an effective amount of a vaccine of this invention.

8 Claims, No Drawings

METHOD OF PREPARING GRAM-NEGATIVE BACTERIAL VACCINES

This application represents the U.S. national phase of PCT/US92/09944, filed Nov. 13, 1992, which is a continuation-in-part of application Ser. No. 07/792,488, filed Nov. 15, 1991, abandoned.

FIELD OF THE INVENTION

The invention relates to the field of Gram-negative bacterial vaccines and their method of production.

BACKGROUND OF THE INVENTION

Vaccines made from Gram-negative bacteria have a well known tendency to cause endotoxic shock. This may result in abortion or death. Gram-negative bacteria release endotoxin from their outer membrane to a slight extent while they are alive, and dividing, but to a far greater extent during and after their death. Bacterial endotoxin is naturally present in tap water, where it is called pyrogen. To avoid the induction of fever, pyrogen-free water for injection is prepared by distillation or other methods of purification. In man the injection of as little as one endotoxin unit (EU) (approximate 0.1 nanogram, or $10^{-10}$ gram) may cause a transient rise in body temperature. In man and other animal, larger doses cause endotoxic shock and death.

The rabbit is similar to man in sensitivity to endotoxin, and the rabbit traditionally has been used to test human injectable products for pyrogenicity. Most other animal species are less sensitive. Horses and pigs are considerably more sensitive than most laboratory rodents. Thus, in the laboratory, only the rabbit is suitable for testing the endotoxic activity of veterinary injectables, although mice can be made relatively sensitive with drugs that alter macrophage function.

In endotoxin assays, the rabbit has largely been replaced by an in vitro test that is even more sensitive. This depends on the action of endotoxin on a fluid extracted from the horseshoe crab (*Limulus amebocyte lysate*, or LAL). The addition of endotoxin in trace amounts causes LAL to gel. Before the gel develops, the transparency of LAL changes in a way that can be measured by a spectrophotometer as increasing optical density.

The free-endotoxin content of cultures of Gram-negative bacteria, killed to make vaccines, varies according to the skill of the manufacturer. One ml. may contain as little as 20 micrograms ($2\times10^{-5}$ gram) or as much as one milligram ($10^{-3}$ gram). Vaccine makers have used several methods to decrease free endotoxin. One involves harvesting the bacterial cells, by centrifuging or filtering, and discarding the endotoxin-rich culture fluid. Another involves adsorbing the cultures with insoluble aluminum (Al) or calcium compounds (carriers) such as aluminum hydroxide gel (Al gel).

Adsorbing with Al gel tends to remove most of the free-endotoxin from solution. Some manufacturers allow the gel, with the endotoxin and other culture products that are absorbed to it, to sediment before decanting the supernatant fluid to remove the remaining free-endotoxin. The bacteria may not be adsorbed to the gel, in which case they usually sediment, leaving the supernatant fluid clear. Decanting has to be delayed until everything has settled and the fluid is clear.

Whether the bacteria have been harvested from the culture, or sedimenting has taken place after adsorbing with an aluminum or calcium compound, the materials are then usually resuspended in a simple aqueous fluid (water, saline, or a buffer solution). Assays will then usually show a disappointing decrease in free-endotoxin content; the change is much less than calculated from the dilution factor on resuspension. This is because endotoxin continues to escape from the bacterial surface, and loosely bound endotoxin becomes desorbed from the carrier.

The two processes are sometimes combined; the bacteria are harvested from the culture medium, resuspended in aqueous fluid, and then adsorbed. It has been shown that adsorbing aqueous suspensions of harvested bacteria with conventional amounts of Al gel produces an undesirable result. For example, when an aqueous suspension of *Salmonella choleraesuis* was adsorbed with Al gel, 25% v/v, there was no detectable free-endotoxin but the ability of the preparation to immunize mice against *S. choleraesuis* was almost completely eliminated. As soon as the gel began to settle, the supernatant fluid was crystal clear, denoting total adsorption.

It was concluded from these observations that a simple aqueous fluid, virtually free of culture medium, would not use up any of the binding capacity of the gel. This would leave the gel in a highly avid state so that anything bindable would be very tightly bound. Thus, all endotoxin was removed from solution but apparently the bacteria were too tightly bound to be released after injection. This evidently interfered with immunization. The observation was repeated with an aqueous suspension of killed *Pasteurella multocida* cells containing toxoid. After adsorption with Al gel, 25% v/v, there was no detectable free-endotoxin but the preparation had a drastically diminished power to induce neutralizing antitoxin in guinea pigs.

The above demonstrates the two extremes of a range of conditions. At one extreme, where Al gel is added to a whole culture, the peptones, and other proteinaceous solutes in the culture fluid, saturate the binding sites on the gel so that a lot of material, including free-endotoxin, is bound loosely or not at all. At the other extreme, where Al gel is added to an aqueous suspension of bacteria, there are almost no proteinaceous solutes to react with the gel and it remains fully avid, tightly binding everything with an affinity for the gel, particularly endotoxin and bacterial cells. In this condition, the tightly bound bacteria and their antigenic products are not free to interact with the cells of a vaccinated animal's immunity system, and immunization is poor.

Thus, there is a need for a method that produces a condition between the extremes of the observed range, where the binding power of the Al gel would be moderate and the adsorption optimal. Most of the endotoxin would be firmly bound, making the vaccine safe, but the binding of bacterial cells and antigens would be loose enough to allow good immunization. This optimal condition would be achieved by suspending the bacteria in a dilution of the culture medium that would appropriately modulate the avidity or affinity of the Al gel. This gave rise to the term affinity-modulated adsorption process, or AMAP®.

Experiments that are the hallmark of AMAP® in its original form were conducted. While keeping the concentration of Al gel constant, in this case 25% v/v, the dilution of culture medium was tinted to achieve optimal adsorption. The end-point of the titration was indicated by a free-endotoxin concentration between 20 and 500 EUs per ml., as assayed by the LAL method.

Experiments with a number of Gram-negative bacteria, including *Salmonella choleraesuis*, *Bordetella bronchiseptica*, and *Pasteurella multocida*, showed that, in the presence of Al gel 25% v/v, the end-point was usually achieved when the culture medium was diluted to give a total concentration of peptones and other proteinaceous materials of about 1% w/v. This usually required diluting the culture medium by a factor of 2.5 to 3.5. Vaccination of animals with the AMAP®-treated materials confirmed that there was no loss of antigenic potency, and no clinical evidence of reactions to endotoxin. The AMAP® optimum had been found.

The SmithKline Beecham Animal Health vaccine sold under the tradename Atrobac 3 (bordetella, pasteurella and erysipelothrix), sold for the prevention of atrophic rhinitis and erysipelas in swine, is the first commercial product made by AMAP®. The process is applied to the two Gram-negative components, bordetella and pasteurella. The product has achieved a good reputation for efficacy and freedom from systemic reactivity (endotoxic shock).

There are other methods of controlling free-endotoxin in Gram-negative bacteria. One consists of a mild alkaline hydrolysis. For example, a culture may be heated at 80° C. and a pH of 10. This treatment inactivates the endotoxin but also destroys many bacterial antigens, especially the proteins.

Another method is fairly effective but has limited application. It consists of the use of glutaraldehyde to inactivate the culture. Glutaraldehyde is a potent cross-linking agent and it binds most of the endotoxin in the culture. After inactivation with glutaraldehyde, bordetella cultures have a free-endotoxin content of roughly 1 microgram ($10^{-6}$ gram) per ml. Glutaraldehyde, however, can be used only in cultures in synthetic growth media. In natural media the proteinaceous solutes bind the glutaraldehyde and prevent its action on the bacteria. The use of glutaraldehyde to make safe bordetella vaccines is described in U.S. Pat. No. 4,888, 169, issued Dec. 19, 1989. "*Bordetella bronchiseptica* vaccine.")

The original version of AMAP® (AMAP®, Mark 1) is characterized by the titration of culture medium against a conventional amount of Al gel to optimally modulate the avidity of the gel. AMAP®, Mark 1, fulfilled the objective of eliminating endotoxic shock without decreasing antigenic potency.

Investigators in this area have recently become acutely aware of a serious problem with all bacterial vaccines containing conventional amounts of Al gel (roughly 10 to 25% v/v), regardless of AMAP® but including products made by AMAP®. These vaccines produce what is called a depot effect. The Al gel, or other mineral carrier, is not readily metabolized, and so it tends to remain in the tissues at the injection site. The bacterial cells and metabolic products adsorbed to the gel are then trapped in the tissues. There they induce chronic irritation leading to granulomas, abscesses, and ultimately scarring. This is especially serious when the vaccine is injected into the muscle of an animal raised for meat. At slaughter the affected cut of meat is often condemned and lost. This is called trim loss due to carcass blemish. The emergence of the injection-site-reaction problem plainly indicated that a new version of AMAP® was needed that would not cause appreciable local reactivity.

SUMMARY OF THE INVENTION

There is provided by this invention a novel method of preparing Gram-negative bacterial vaccines comprising providing a concentrated Gram-negative bacterial antigenic preparation, adsorbing the preparation with a mineral carrier capable of binding free-endotoxin in the antigenic preparation in an amount effective to produce optimal binding of endotoxin and antigen and diluting the adsorbed preparation for use in a vaccine, whereby the amount of mineral carrier in the vaccine is less than if the mineral carrier had been added to an unconcentrated antigenic preparation or to the final vaccine.

Also provided by this invention is a vaccine produced by the method of this invention.

Further provided by this invention is a Gram-negative bacterial vaccine wherein the improvement comprises a concentration of mineral carrier in the vaccine which is less than 5.0% v/v.

Further provided by this invention is a Gram-negative bacterial vaccine comprising a mineral carrier wherein the amount of the mineral carrier in the vaccine has been predetermined by a method comprising providing a concentrated Gram-negative bacterial antigenic preparation, adsorbing the preparation with a mineral carrier capable of binding free-endotoxin in the antigenic preparation in an amount effective to produce optimal binding of endotoxin and antigen and diluting the adsorbed preparation for use in a vaccine, whereby the amount of mineral carrier in the vaccine is less than if the mineral carder had been added to an unconcentrated antigenic preparation or to the final vaccine Further provided by this invention is a method of vaccinating an animal against Gram-negative bacterial infections comprising administering to the animal an effective amount of a vaccine of this invention.

DETAILED DESCRIPTION OF THE INVENTION

This invention solves the aforementioned problem in the prior art methods. According to this invention, endotoxin can be controlled in concentrated antigenic preparations of Gram-negative bacteria by adding a fairly high concentration of mineral carrier to the antigenic preparations. When the preparation is diluted with, e.g. water or saline to the density required in a vaccine, the final concentration of mineral carrier is substantially reduced and the endotoxin surprisingly remains firmly bound. The vaccines produced by the method of this invention have proved to have good efficacy, excellent systemic safety, and only slight injection-site reactivity in vaccinated animals.

"Concentrated Gram-negative bacterial antigenic preparation" as referred to herein means antigenic preparations that have a much higher antigen content than the final vaccine. Generally, the concentrated preparation has an antigen concentration at least about ten times higher and preferably forty to fifty times higher than the antigen concentration of the final vaccine. The upper limit on concentration is governed by ability to work with the preparation, i.e., it should not be so thick that it is difficult to work with. The lower limit is governed by the desire to reduce the final concentration of mineral carrier in the vaccine. In some cases, the unconcentrated culture fluids or their fractions will meet this criterion without resort to concentration. However, in most cases the fluids must be concentrated. These can be prepared by centrifugation or others methods known to those in the art. The more the antigenic preparation is concentrated, the more it will be diluted during assembly of the vaccine and the lower the concentration of carrier in the final reconstituted vaccine. The preferred concentration of the bacterial antigenic preparation is such that when the preparation is adsorbed and assembled into a final vaccine the mineral carrier concentration will be less than 5.0% v/v and preferably less than 3.0% v/v.

Surprisingly, Gram-negative bacterial antigenic preparations include for example, whole bacterial suspensions as well as bacterial extracts, and bacterium-free culture fluids. In the past, AMAP® was demonstrated to be suitable for whole bacterial preparations only.

Examples of Gram-negative bacteria that can be used in the invention include, Salmonella, E. coli, Shigella, Campylobacter, Fusobacterium, Bordetella, Pasteurella, Actinobacillus, Haemophilus and Histophilus.

Suitable mineral carriers include those capable of binding the free-endotoxin of Gram-negative bacteria. Examples include aluminum hydroxide, aluminum phosphate, an alum, or calcium phosphate. The mineral carrier is added to the concentrated antigenic preparation in an amount effective to reduce the concentration of free-endotoxin in the mineral carrier/antigenic preparation. Effective amount means the amount necessary to bind endotoxin tightly and to reduce free-endotoxin to a safe level to administer yet not so high an amount as to bind the antigens too tightly and thereby inhibit the antigenic stimulus. The effective amount represents a compromise between macromolecular excess and carrier excess. This balance is indicated by a free-endotoxin level in the adsorbed preparation of about 20 to about 1000 EU per ml, preferably about 20 to about 500 EU per dose.

The FIG. 20 to 500 EU per ml has no relevance to the final vaccine. Generally, the free-endotoxin amount will remain within this range but depending upon the influence of other components, it may approach 1000 EU per ml in the final vaccine and still be acceptable. The increase is probably attributable to endotoxin displaced from the gel by macromolecules in other components (Gram-positives, viruses etc.). This is not believed to affect safety as it has been shown that most domestic animals can tolerate vaccines containing endotoxin in amounts up to 10,000 EU per ml.

During vaccine development, the degree of concentration of the antigenic preparation is established, and the amount of mineral carrier is determined on several experimental batches. This sets the proportion of carrier to be added to the concentrate during manufacture.

The antigenic preparation is the agent that modulates the avidity of the mineral carrier by its constituent molecules attaching to the binding sites of the carrier or competing for binding sites on the carrier with the endotoxin. This takes place while the carrier is being added. The avidity that remains determines how much endotoxin gets bound and how tightly. The more carrier that is added, the more free binding sites are left and the less free endotoxin you can assay at the end. Where carrier is added beyond the endpoint, an excess of binding sites develops and all macromolecules with an affinity for the carrier will be tightly bound. Free-endotoxin will be zero but the binding of antigens may be so tight as to inhibit the antigenic stimulus by the specific immunogens.

In the method of this invention, when bacterial cells are used, generally at least 90% of the culture medium is discarded while concentrating. Accordingly, the culture should be managed and inactivated in a manner that minimizes the loss of protective antigens (immunogens) from the bacteria to the medium. This requires, first, that the inactivating agent, when used, should be added when the culture is still in the exponential ("logarithmic") phase of the growth cycle. At this stage, virtually 100% of cells are alive and dividing and, accordingly, their structural integrity is complete. As soon as the growth rate slows (the transition phase), increasing numbers of bacteria are dead or dying and beginning to disintegrate, shedding both antigens and endotoxin. The inactivating agent should preferably be a fixative, i.e, an agent that binds the cellular structure and prevents disintegration.

Formaldehyde solution (formalin) is the most broadly useful inactivating agent. Formalin permits some release of endotoxin during the killing of the bacterial cells but this is easily removed from solution by the method of this invention. Once the culture is inactivated, there is little further loss. Glutaraldehyde is even more effective, binding endotoxin that is already free in the culture medium; free-endotoxin actually decreases during inactivation. As discussed above, however, glutaraldehyde can be used only in cultures in completely synthetic media.

The preparation may be diluted for use as a vaccine. The vaccine may contain other ingredients such as adjuvants, additional mineral carriers and a variety of other antigens as is known to those in the art.

In another aspect of this invention, there is provided a method of vaccinating animals against Gram-negative bacterial infections comprising administering to the animal an effective amount of the vaccine of this invention. An effective amount of vaccine is that amount capable of eliciting immunity. The effective amount will vary with the antigen and can be readily determined by one of skill in the art.

The following examples illustrate the preparation of exemplary vaccines from Gram-negative bacteria using the method of the invention, and the safety and efficacy of these vaccines. These examples are illustrative only and do not limit the scope of the invention

EXAMPLE 1

Preparation of E. coli Vaccine

E. coli, strain NADC 1471 (pilus type K99) from the National Animal Disease Center, Ames, Iowa is grown in the synthetic medium described below at 37° C., with aeration, for 16 to 32 hours on agar plates or 12 to 32 hours in flasks.

The production growth cycle is from 4 to 12 hours with controlled agitation. The synthetic culture medium for growing E. coli is prepared as follows: 2.0 g $NH_4Cl$, 4.50 g $KH_2PO_4$, and 17.0 g $Na_2HPO_4$ are combined in distilled water, the pH is adjusted to 7.4±0.2 units with NaOH and the mixture sterilized by autoclaving. Solutions of $MgSO_4.7H_2O$ (0.05 g), $FeSO_4.7H_2O$ (5.0 mg), and glucose (5.0 g) are each prepared separately as concentrates, sterilized by filtration and added to the base medium. If required, a nutritional supplement is added to the fermentor culture during the growth cycle. The supplement provides ingredients in the following maximum amounts per liter of fermentor culture: 9.12 g $KH_2PO_4$, 34.0 g $Na_2HPO_4$, 1.0 g $MgSO_4.7H_2O$, 0.1 g $FeSO_4.7H_2O$, and 15.0 g Glucose. The $KH_2PO_4$ and $Na_2HPO_4$ are combined in distilled water and sterilized by autoclaving. The solutions of $MgSO_4.7H_2O$, $FeSO_4.7H_2O$, and glucose are each prepared separately as concentrates, and sterilized by filtration.

To inactivate the culture according to this method, the inactivating agent, formalin (Formaldehyde Solution USP) is added to the culture to give a concentration of about 0.5% v/v. The culture is inactivated overnight in the fermentor at 37° C.±1° C., with low-speed stirring.

For the concentrating step, the inactivated culture is passed through a Sharples continuous flow centrifuge, which sediments the bacteria as a paste. Alternatively, the bacteria may be concentrated by ultrafiltration under standard conditions. The bacteria are concentrated to a value that is ten time the concentration in the finished vaccine, i.e., $1 \times 10^{10}$ bacteria per mL. The bacterial count of the concentrate may be determined by either the Petroff-Hauser method or Coulter counter. The concentrate is then diluted by adding phosphate-buffered saline (PBS), pH 7.2±0.2, so that an immunogenic amount, or antigen dose, is contained in 0.2 mL, the final dose volume being 2 mL.

By titration at pH 6.5 it was determined that the addition of Rehydragel™ carrier to a final 20% v/v resulted in a free-endotoxin value of 270 EUs per mL (mean of 3 batches) in the concentrate. This value is within the most preferred range of 20 to 500 EUs per mL chosen as the end-point of the titration. This amount of carrier is thus added to the concentrated suspension and adsorption occurs.

To prepare a vaccine composition, 12.5 mL of the resulting adsorbed concentrate is diluted with PBS to a final volume of 100 mL. The volume of 12.5 mL consists of 10 mL of the resuspended bacteria and 2.5 mL of the gel. In the vaccine, accordingly, the original cell suspension is diluted by the required factor of 10 (0.2 mL in a 2 mL dose) and the gel is present at a final concentration of 2.5% v/v, meeting the most desirable standard of <3% v/v. Merthiolate 10% solution is added to the assembled serial as a preservative. Final concentration of merthiolate does not exceed 0.01% weight per volume.

Antigenicity of a vaccine prepared as described above was tested as follows. Twenty mice were each injected subcutaneously with 0.2 mL of a 20-fold dilution of the vaccine, i.e., one four-hundredth of the cattle dose. At three weeks, the mice were bled. Serum samples from the mice were individually filtrated in an agglutination test against an inactivated antigen prepared from *E. coli* strain 1471 having K99 pili. Their sera had a geometric mean agglutination titer of 13.

EXAMPLE 2

Preparation of *A. pleuropneumoniae* Vaccine

*Actinobacillus pleuropneumoniae*, serotype 1 (strain Schelkopf; Dr. Schultz, Avoca, Iowa), serotype 5 (strain K-17; Dr. Schultz; Avoca, Iowa) and serotype 7 (strain WF-83; SmithKline Beecham Corporation) were prepared for use in a vaccine by the method of the invention. The three *A. pleuropneumoniae* strains were cultured in liquid medium [Gibco Laboratories, Bacterin HP Medium, Formula #90-5066] at 37°±1° C. for 4 to 24 hours. The dissolved oxygen value of 30% was controlled by aeration with sterile air and by agitation. Sterile antifoam solution was used to control foam and was added before the medium was inoculated. The pH of the culture was maintained at 7.3±0.2 by the addition of sterile 5N NaOH or 4N HCl.

At the end of exponential growth, each culture was chilled to a temperature of 20° C. to arrest growth. The chilled culture was centrifuged and the sediment collected as a very dense suspension of bacteria. The suspension was heated at 56°±1° C. with agitation for one hour. The suspension was then centrifuged, and the supernatant fluid (extract) collected. Sterile 10% merthiolate and 10% ethylenediamine tetraacetic acid (EDTA) solutions were added as preservatives at final concentrations of 0.01% and 0.07% (weight per volume), respectively. The extracts were passed through sterile 0.45 and 0.3 µm filters and stored at 2° C.–7° C. until assembled.

A vaccine was prepared as follows. The carbohydrate content of each extract was determined by the phenol method, and protein by the Lowry method. The molecules in the extract were then coupled or linked by reaction with glutaraldehyde. A 25% solution of glutaraldehyde was added to the extracts at the rate of 1 mL per gram of total protein. To neutralize any residual glutaraldehyde, a solution of lysine was then added to the extract at the rate of 12.5 mg of lysine per mL of the glutaraldehyde solution. This mixture was incubated at room temperature for two hours with agitation and stored at 4° C. overnight.

Extracts of the three serotypes were combined according to their carbohydrate assay value, so that a 2 mL dose of vaccine contained 20 µg of carbohydrate of each serotype (10 µg/mL). Before absorbing with aluminum hydroxide gel the volume of the combined concentrate was adjusted to ¼oth of the final volume of the batch. This required the addition of a small volume of PBS.

A titration showed that when Rehydragel™ carrier was added at pH 6.5 to the adjusted concentrate at the rate of 39 mL gel per 100 mL concentrate, to give a final 28% v/v, free-endotoxin was decreased to 470 EU per mL, within the desired range of 20 to 500 EU per mL.

To make one liter of product, a sufficient amount of each serotype was added to the vessel toy contribute 10,000 µg (10 mg) carbohydrate. PBS was added to bring the volume to 25 mL. Rehydragel™ carrier was then added in a volume of 9.75 mL (39% of 25 mL). The pH was adjusted to 6.5 and the mixture was stirred for 1 hour at room temperature. A 40% emulsion of Amphigen adjuvant [Hydronics, Inc.] was added next in a volume of 125 mL (one eighth of the final volume), to give a final 5% v/v Amphigen adjuvant in the vaccine. The volume was then increased to 1 liter by the further addition of PBS. The final concentration of Rehydragel™ carrier was thus 0.98% v/v, a very desirable value for the avoidance of tissue reactions at the injection site.

EXAMPLE 3

Safety and Efficacy of *A. pleuropneumoniae* Vaccines

This example illustrates the safety and efficacy of vaccines prepared according to the method described in Examples 2.

A. Safety

Two vaccines were made from the same set of extracts as described in Example 2 above. One was prepared by the process of the present invention, i.e., adsorbing the glutaraldehyde-coupled antigenic material with Rehydragel™ carrier as described in Example 2 (Product A). The other was prepared from the glutaraldehyde coupled material with an additional 9.75 mL of PBS in place of the aluminum hydroxide carrier (Product B ). As placebo, a mixture was prepared that consisted of Amphigen adjuvant, 5%, in PBS.

Weaned (3–4 week old) pigs were randomly assigned to three groups and injected intramuscularly in the side of the neck with one of these three products. Each pig received two (2) mL doses of the appropriate vaccine at a three-week interval. Pigs were assigned to the products in the following numbers: Product A (65), Product B (35), and Placebo (40).

When assayed with the chromogenic LAL test, the Product A was found to have a free-endotoxin content of 0.546 µg per dose (measured after dilution) and the Product B 9.636 µg per dose. For *A. pleuropneumoniae* vaccines, it is desirable to have endotoxin levels less than about 1 µg per dose. In Group A, the pigs receiving vaccine prepared by the method of the present invention, one of the 65 pigs showed transient labored breathing after the first dose only. The rest of the group showed no systemic reactions. In Group B, given the conventional vaccine, most of the pigs developed typical endotoxic shock, characterized by stiffness, dyspnea, and depression, during a period of 2 to 3 hours following vaccination. Of the 35 pigs in Group B, shock was seen in 30 after the first injection and in 8 after the second injection. The placebo group show/ed no systemic reactions.

None of the pigs in any group had local reactions detectable clinically or at autopsy.

B. Efficacy

The immunity of the pigs was challenged intranasally (controls last) with live virulent cultures (0.5 mL per nostril) of either serotype 1, strain Schelkopf ($1.74 \times 10^9$ colony forming united (CFU)/mL), serotype 5, strain K×17 ($7.1 \times 10^7$ CFU/mL), or serotype 7, strain WF 83 ($1.55 \times 10^9$ CFU/mL), one week after the second vaccination. Prior to challenge, three pigs had died from unrelated causes in Group A, four in Group B, and six in the placebo group. Pigs that died during the days following challenge were subjected to autopsy as soon as possible. Survivors were killed and examined at 7 to 8 days.

At autopsy, the lungs of each pig were weighed. Pneumonic lesions were then excised and weighed and the lesion weight was calculated as a percentage of total lung weight. Separately, the pigs were scored according to a scale of severity for suppurative pneumonia, fibrinous pleuritis, and serous fluid in the thoracic cavity. The results are summarized in the following table.

Statistical analysis (Mann-Whitney U test) of the percent lung damage of pigs challenged with each serotype showed a significant difference ($\alpha=0.05$) between Group A and the placebo group and Group B and the placebo group, as reported in Table I below. Statistical analysis (Mann-Whitney U test) of associated lung lesion scores also showed a significant difference between Group A and the placebo group and Group B and the placebo group. The small differences in percent damage and lesion score, between Groups A and B, were not significant.

TABLE 1

| Challenge serotype | Mean values at autopsy | | |
|---|---|---|---|
| | Vaccine | Lesion % | Lesion score |
| 1 | Group A | 41 | 2.5 |
| | Group B | 38 | 2.7 |
| | Placebo | 84 | 5.3 |
| 5 | Group A | 39 | 2.6 |
| | Group B | 38 | 2.2 |
| | Placebo | 78 | 5.1 |
| 7 | Group A | 32 | 1.8 |
| | Group B | 24 | 1.4 |
| | Placebo | 72 | 4.7 |

These results show that vaccine A, which was prepared according to the invention, was just as efficacious as the conventional vaccine B and equally free from injection-site reactions. However, in contrast with the conventional vaccine, which induced endotoxic shock in most of the pigs, vaccine A proved to be almost totally free of systemic reactivity; the transient labored breathing in one of the 65 pigs was not believed to be typical of endotoxic shock.

In summary, the process of this invention achieved the desired effect of eliminating endotoxic shock without loss of efficacy and, significantly, without introducing unacceptable injection site reactions.

Numerous modifications and variations of the present invention are included in this specification and are expected to be obvious to one of skill in the art. Such modifications and alterations and processes of the present invention am believed to be encompassed in the scope of the claims appended hereto.

We claim:

1. A method of preparing a Gram-negative bacterial vaccine, comprising:

(a) providing a concentrated Gram-negative bacterial antigenic preparation which comprises antigen, and free endotoxin in an amount sufficient to induce endotoxic shock when administered to an animal;

(b) adding to the antigenic preparation of (a) a concentration of mineral carrier in an amount effective to reduce the free endotoxin to a level that will not trigger endotoxic shock, but in which the antigen remains sufficiently available to trigger an immunological response;

(c) diluting the preparation of (b) so that the concentration of mineral carrier is less than 5% (v/v), but the free endotoxin remains at a level that will not trigger endotoxic shock, and the concentration of available antigen is sufficient to trigger an immunological response; and (d) recovering the diluted preparation of (c) for administration as a vaccine.

2. The method of claim 1 wherein the effective amount of mineral carrier is indicated by a free-endotoxin concentration in the preparation of step (b) in the range of 20 to 1000 endotoxin units per ml.

3. The method of claim 1 wherein the mineral carrier is an aluminum hydroxide gel.

4. The method of claim 1 wherein the Gram-negative bacterial antigenic preparation comprises *E. coli*.

5. The method of claim 1 wherein the Gram-negative bacterial antigenic preparation comprises *Actinobacillus pleuropneumoniae*.

6. The method of claim 1 wherein the concentrated antigenic preparation is at least ten times as concentrated as it is in the final vaccine.

7. An improved Gram-negative bacterial vaccine comprising antigen endotoxin in a concentration otherwise capable of inducing endotoxic shock when administered to an animal, and a mineral carrier, in which a sufficient amount of the endotoxin is bound to the mineral carrier in the vaccine so as to prevent the vaccine from triggering endotoxic shock wherein the improvement comprises a concentration of the mineral carrier in the vaccine which is less than 5% (v/v).

8. A method of vaccinating an animal against Gram-negative bacterial infections comprising administering to the animal an effective amount of the vaccine of claim 7.

* * * * *

UNITED STATES PATENT AND TRADEMARK OFFICE
CERTIFICATE OF CORRECTION

PATENT NO. : 5,616,328
DATED : April 1, 1997
INVENTOR(S) : Roberts, et al

It is certified that error appears in the above-indentified patent and that said Letters Patent is hereby corrected as shown below:

In column 2, line 61, "tinted" should instead read --titrated--.

In column 4, line 24, "carder" should instead read --carrier--.

In column 5, line 28, "The FIG. 20" should instead read --The figure 20--.

In column 8, line 29, "toy" should instead read --to--.

In column 9, line 15, "show/ed" should instead read --showed--.

In column 10, line 53, in claim 7, "antigen endotoxin" should instead read --antigen, endotoxin--; on line 58, "shock wherein" should instead read --shock, wherein--.

Signed and Sealed this

Twenty-second Day of July, 1997

Attest:

Attesting Officer

BRUCE LEHMAN

Commissioner of Patents and Trademarks